United States Patent
Thuillier et al.

[11] 3,935,203
[45] Jan. 27, 1976

[54] DERIVATIVES OF 3-OXO-2,3-DIHYDRO-1,4-BENZOXAZINE

[75] Inventors: Germaine Thuillier, Paris; Jacqueline Laforest, Vincennes, both of France

[73] Assignee: CERPHA, Arceuil, France

[22] Filed: Aug. 2, 1973

[21] Appl. No.: 384,924

[30] Foreign Application Priority Data
Aug. 3, 1972 France .................. 72.28095

[52] U.S. Cl............... 260/244 R; 424/248; 260/573
[51] Int. Cl.² ........................................ C07D 265/28
[58] Field of Search .................................... 260/244

[56] References Cited
UNITED STATES PATENTS

| | | | |
|---|---|---|---|
| 3,354,209 | 11/1967 | Brack .................................. | 260/573 |
| 3,453,270 | 7/1969 | Weaver et al....................... | 260/244 |
| 3,557,103 | 1/1971 | Nordin............................... | 260/244 |
| 3,644,350 | 2/1972 | Helsley .............................. | 260/244 |
| 3,715,353 | 2/1973 | Krapcho ............................ | 260/244 |

Primary Examiner—Harry I. Moatz

[57] ABSTRACT

The invention relates to new derivatives of 3-oxo-2,3-dihydro-1,4-benzoxazine corresponding to the general formula

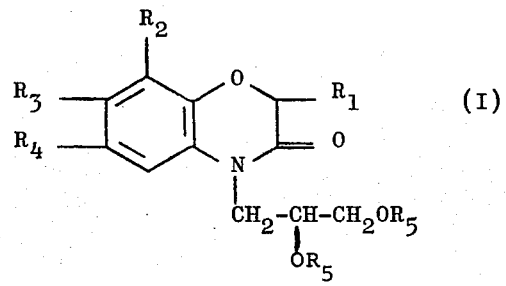

in which
$R_1$ is selected from the group consisting of the hydrogen atom and a lower alkyl group;
$R_2$, $R_3$ and $R_4$ which are identical or different, are selected from the group consisting of the hydrogen atom, a halogen atom, a nitro group, a lower alkyl group, a lower alkoxy group and $R_4$ may be an allyl group;
$R_5$ is selected from the group consisting of the hydrogen atom and an acyl group, preferably acetyl. These derivatives can be used for therapeutic purposes, more especially as analgesics and anti-oedematous agents.

17 Claims, No Drawings

DERIVATIVES OF 3-OXO-2,3-DIHYDRO-1,4-BENZOXAZINE

This invention relates to new derivatives of 3-oxo-2,3-dihydro-1,4-benzoxazine, to methods for their preparation and to their therapeutic applications, more particularly as anti-oedematous and analgesic agents.

The 3-oxo-2,3-dihydro-1,4-benzoxazine derivatives obtained in accordance with the invention correspond to the following general formula:

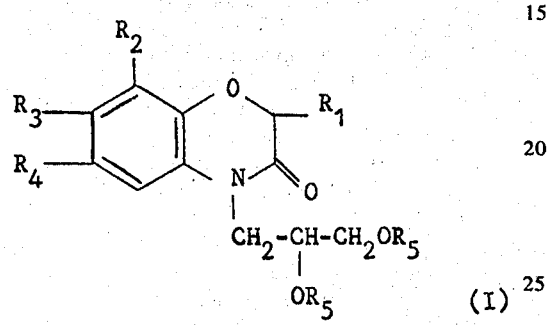

in which:
  $R_1$ represents the hydrogen atom or a lower alkyl group;
  $R_2$, $R_3$ and $R_4$, which are identical or different, each represent the hydrogen atom, a halogen atom, a nitro group, a lower alkyl group, a lower alkoxy group or a lower alkylidene group; $R_5$ represents the hydrogen atom or an acyl group, preferably acetyl.

In the context of the invention, lower alkyl, alkoxy and alkylidene groups are groups containing at most 5 carbon atoms. Halogen atoms are the atoms of fluorine, chlorine, bromine or iodine.

The new derivatives according to the invention can be prepared by an entirely general process in which the alkali salt of a 3-oxo-2,3-dihydro-benzoxazine of the formula

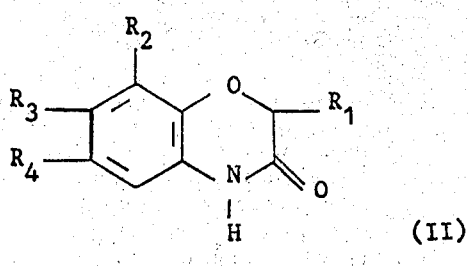

in which $R_1$, $R_2$, $R_3$ and $R_4$ are as defined above, is reacted with a propanol derivative of the formula

in which $R_5$ is as defined above; X represents a halogen atom and Y represents $OR_5$, X and Y together can represent the oxygen atom and can form an epoxy group with the carbon atoms to which they are attached, the alkali salt can be obtained by the action of a base, such as an alkali alcoholate or hydroxide, sodium amide or hydride, depending upon the nature of the reaction medium; solvents such as aqueous or non-aqueous alcohols, benzene hydrocarbons or polar aprotic solvents can be used, and the reaction can be carried out at a temperature between 20°C and the reflux temperature of the aforementioned solvent.

Instead of substituting the nitrogen of the lactam, it is also possible to prepare the derivatives according to the invention from an N-alkylaminophenol of the formula

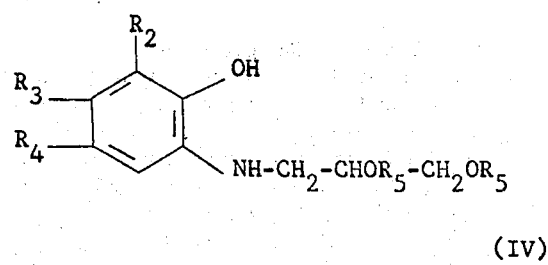

in which $R_1$, $R_2$, $R_3$, $R_4$ and $R_5$ are as defined above, by the action of an α-halogenated acid derivative and, in particular, by the action of a compound of the formula

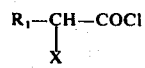

where X and $R_1$ are as defined above, followed by the action of a base or even by the action, in the presence of a base, of a compound corresponding to the formula

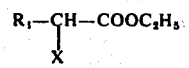

in an apolar solvent under reflux with elimination of the alcohol formed, or in a polar aprotic solvent. Those compounds in which $R_5$ represents an acyl group can also be obtained by the action of an acid derivative, such as a chloride or anhydride, on the corresponding dihydroxylated derivatives.

More particularly, the new derivatives of formula I can be prepared by various methods, applications of known principles and in particular, in the case of compounds where $R_5$ represents the hydrogen atom A. by the action of the alkali salt of a 3-oxo-2,3-dihydro-1,4-benzoxazine corresponding to the formula

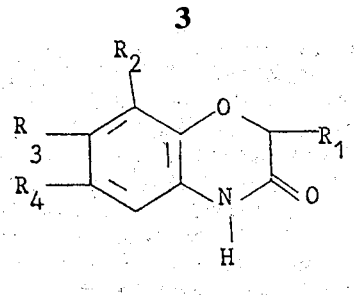

(II)

in which $R_1$, $R_2$, $R_3$, $R_4$ are as defined above, of a halogenated derivative of the formula

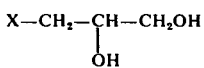

where X represents a halogen atom.

The salt can be obtained by the action of a base such as an alkali alcoholate or hydroxide, sodium amide or sodium hydride, and the reaction can be carried out in various solvents such as aqueous or non-aqueous alcohols, benzene hydrocarbons or polar aprotic solvents.

B. by the action on the alkali salt of a 3-oxo-2,3-dihydro-1,4-benzoxazine defined as above, of 2,3-epoxy propanol in an alcoholic solvent such as ethanol.

C. by the action on a N-alkylaminophenol corresponding to the formula

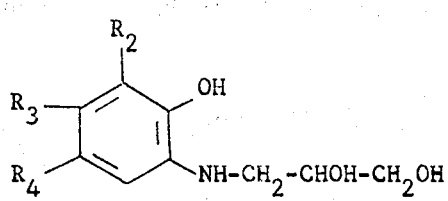

of an α-halogenated acid chloride corresponding to the formula

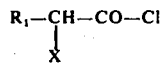

where X, $R_1$, $R_2$, $R_3$ and $R_4$ are as defined above, the intermediate amidophenol being cyclised in the presence of a base in various solvents such as alcohols, ketones and the like.

D. by the action on the alkali salt of an N-alkylaminophenol defined as above of an α-halogenated ester of the formula

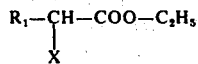

in an apolar solvent under reflux with elimination of the ethanol formed, or in a polar aprotic solvent; cyclisation of the intermediate aminophenoxy ether is carried out at the same time as condensation.

In the case of compounds where $R_5$ represents an acyl group

E. by the action of the corresponding dihydroxylated derivatives of an acid derivative such as, in particular, an acid anhydride and acid chloride.

F. by the action on the alkali salt of a 3-oxo-2,3-dihydro-1,4-benzoxazine of a halogenated derivative corresponding to the formula

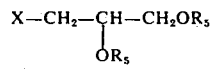

where X represents a halogen atom and $R_5$ represents an acyl group.

The invention is illustrated by but by no means limited to the following Examples of preparation. All the products of formula I can be worked up by any of the methods referred to earlier on.

In these Examples, the melting points were measured in capillary with a Gellenkamp apparatus. Each of the compounds described was subjected to elemental analysis, and the results correspond to the normally accepted standards. The structure of the products prepared was confirmed by studying the infrared and nuclear magnetic resonance spectra.

EXAMPLE 1

2-methyl-3-oxo-4-(2,3-dihydroxy propyl)-6-chloro-2,3-dihydro-1,4-benzoxazine

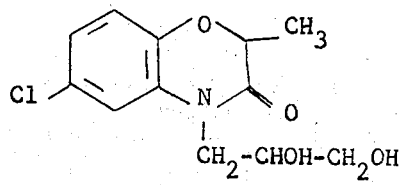

a. Method A 80 ml of a solution of sodium ethylate prepared with 1.15 g of sodium, are added to a suspension of 9.85 g of 2-methyl-3-oxo-6-chloro-2,3-dihydro-1,4-benzoxazine in 120 ml of absolute ethanol which is then heated slowly to and kept for 30 minutes at reflux temperature. 50 mg of potassium iodide and 5.7 g of 3-chloro-1,2-propane diol are then added to the solution after cooling, and the medium again heated slowly to reflux and kept under reflux for several hours until it is neutral.

After cooling, the sodium chloride precipitated is isolated, and the solvent and volatile products removed under reduced pressure.

In order to eliminate most of the unreacted starting products, the residue can be dissolved at 85°C in a minimal quantity of toluene and the organic phase washed first with hot aqueous solutions of soda (0.5 N) and then with water. After cooling and drying of the organic solution, the solvent is evaporated under reduced pressure and the solid residue recrystallised from isopropyloxide.

Purification can also be carried out by chromatography in a silica column with methylene chloride as the eluent. Pure 2-methyl-3-oxo-4-(2,3-dihydroxypropyl)-6-chloro-2,3-dihydro-1,4-benzoxazine is obtained in a yield of 60 % by this method in the form of a white solid with a melting point of 88°C.

The reaction can also be carried out in 95% ethanol under reflux, the alkali salt of the lactam being prepared by the action of potash. 17 g of the required products are obtained from 15 g of benzoxazine and 11 g of chloropropane diol.

If the reaction is carried out in dimethyl formamide, ambient temperature (20°C) is applied and the salt of the lactam is prepared by the action of one equivalent either of sodium ethylate or of sodium hydride, the chloropropane diol being introduced into the medium in a stoichiometric proportion after formation of the salt.

In toluene, the reaction is carried out at the reflux temperature of the solvent and the salt of the lactam is prepared by the action of sodium amide or a sodium alcoholate; in the second case, the alcohol liberated is eliminated before introduction of the halogenated derivative. Irrespective of the procedure adopted, the end product is obtained in substantially equivalent yields.

b. Method B 4 g of soda in pellet form are added to a lukewarm solution of 19.6 g of 2-methyl-3-oxo-6-chloro-2,3-dihydro-1,4-benzoxazine in 140 ml of ethanol, and the resulting mixture heated for 1 hour to the reflux temperature of the solvent. 11.1 g of 2,3-epoxy propanol are poured into the orange-coloured solution obtained after cooling, and the resulting solution slowly heated to the reflux temperature of the reaction medium which is maintained for a few hours. After cooling, the medium is neutralised by the addition of mineral acid and the solvents are evaporated under reduced pressure. The residue is dissolved in a water-imiscible solvent (ethyl ether, chloroform . . . ), and the organic phase washed first with an aqueous solution of soda (2 N), and then with water. The pure product, obtained after several recrystallisations from methylene chloride or benzene, melts at 88°C. Yield 65 %.

EXAMPLE 2

2-ethyl-3-oxo-4-(2,3-dihydroxy propyl)-6-chloro-2,3-dihydro-1,4-benzoxazine

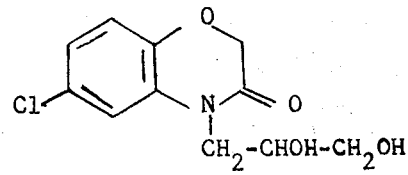

Method A (solvent toluene)

73.5 g of 2-ethyl-3-oxo-6-chloro-2,3-dihydro-1,4-benzoxazine are dissolved under heat in 650 ml of toluene followed by the gradual addition with stirring of 19.7 g of sodium methylate, the methanol formed being continuously distilled off. One hour after the end of the addition, 43 g of 3-chloro-1,2-propane diol are introduced, and the reflux maintained for 4 hours. The precipitate formed is filtered and washed with water. The solvent is evaporated in vacuo and the solid obtained, to which the precipitate previously isolated is added, is recrystallised from methylene chloride. After this first recrystallisation, the product still contains some of the starting lactam. It can be eliminated either by several recrystallisations from toluene or by treatment with soda.

The mixture is dissolved in methylene chloride at ambient temperature and the organic phase treated with an aqueous solution of soda (5 N). The white precipitate formed is isolated, washed with methylene chloride and taken up in 1 part of water and 2 parts of methylene chloride. If necessary, the mixture is neutralised by the action of a dilute acid.

The organic phase is decanted, bleached on animal black and the solvent eliminated under reduced pressure. The pure product melts at 80°C. Yield: 50 %.

14.5 g of sodium amide can be used instead of sodium methylate in this operation. In this case, the medium is heated for 1.5 hours to the reflux temperature before addition of the chlorinated derivative.

EXAMPLE 3

3-oxo-4-(2,3-dihydroxypropyl)-6-chloro-2,3-dihydro-1,4-benzoxazine

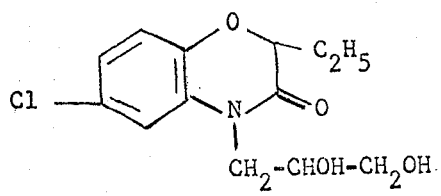

Method A (solvent dimethyl formamide)

28 g of 3-oxo-6-chloro-2,3-dihydro-1,4-benzoxazine are added to a solution of sodium ethylate in 500 ml of ethanol prepared with 3.7 g of sodium, and the mixture heated for 1 hour to the reflux temperature. 300 ml of dry dimethyl formamide are poured into the resulting solution and the ethanol eliminated under reduced pressure.

12.5 ml of 3-chloro-1,2-propane diol are then added, followed by heating for 2 hours to a temperature of 80°C which is maintained until the solution is neutral, i.e. for about 1 hour.

After cooling, the sodium chloride formed is filtered and the solvent eliminated under reduced pressure whilst avoiding any overheating of the medium. After recrystallisation from toluene, pure 3-oxo-4-(2,3-dihydroxy propyl)-6-chloro-2,3-dihydro-1,4-benzoxazine, m.p. 115°C, is obtained in a yield of 50 %.

EXAMPLE 4

2-methyl-3-oxo-4-(2,3-dihydroxy propyl)-6-chloro-7-bromo-2,3-dihydro-1,4-benzoxazine

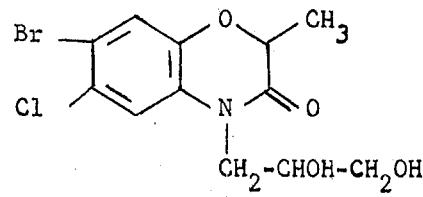

This compound is synthesised in a yield of 75 % by applying Method A (solvent ethanol), followed by recrystallisation from aqueous ethanol (95 %) m.p. 158°C.

EXAMPLE 5

2-methyl-3-oxo-4-(2,3-dihydroxy propyl)-6-methyl-2,3-dihydro-1,4-benzoxaine

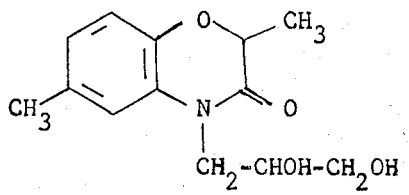

This product is obtained in a yield of 55 % by Method A using dimethyl formamide as solvent (recrystallisation from petroleum ether), m.p. 76°C.

EXAMPLE 6

2-methyl-3-oxo-4-(2,3-dihydroxy propyl)-6-n-propyl-8-methoxy-2,3-dihydro-1,4-benzoxazine

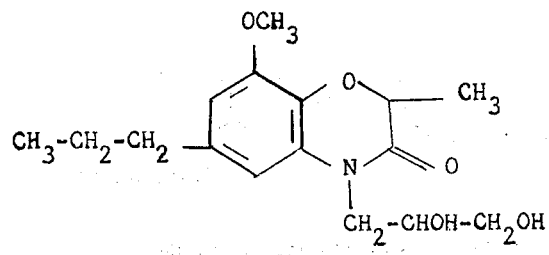

This compound was obtained in a yield of 55 % by Method A using dimethyl formamide as solvent (recrystallisation from isopropyloxide), m.p. 93°C.

EXAMPLE 7

2-methyl-3-oxo-4-(2,3-dihydroxy propyl)-6-nitro-2,3-dihydro-1,4-benzoxazine

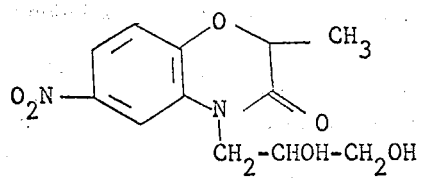

This compound is prepared in a yield of 50 % by Method A using dimethyl formamide as solvent (recrystallisation from benzene), m.p. 96°C, or by Method C described below.

Method C

A mixture of 35 g of 2-amino-4-nitrophenol, 38.7 g of 3-bromo-1,2-propane diol and 34.5g of potassium carbonate in 300 ml of toluene is heated with stirring to reflux over a period of 16 hours. After filtration of the hot solution, the phenol is extracted from the organic phase in an aqueous soda solution (2 N). This is followed by acidification with 5 N hydrochloric acid and washing with ether. After neutralisation by the addition of a 10 % sodium bicarbonate solution, the end product is extracted with chloroform.

The organic phase is washed with water and dried over sodium sulphate, after which the solvent is evaporated under reduced pressure. 12.7 g of 2-chloropropionyl chloride in solution in 50 ml of chloroform are then added dropwise to a solution of 11 g of the product previously obtained in 200 ml of chloroform kept at a temperature below 0°C. On completion of the addition, the mixture is allowed to return slowly to ambient temperature. The solution is then poured into one volume of water. The organic phase is decanted, washed with water until neutral, dried over magnesium sulphate and the chloroform evaporated. The solid obtained is added to 300 ml of a solution of sodium ethylate, prepared with 2.3 g of sodium, and the mixture heated for 4 hours to reflux. After cooling and separation of the precipitate, the solution is washed with soda and then with water, dried over magnesium sulphate and the solvent evaporated under reduced pressure. The product obtained is purified by successive recrystallisations from benzene (yield: 30 %), m.p. 96°C.

EXAMPLE 8

2-ethyl-3-oxo-4-(2,3-dihydroxy propyl)-2,3-dihydro-1,4-benzoxazine

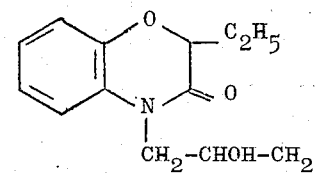

This compound is prepared in a yield of 35 % by Method A using ethanol as solvent (recrystallisation from cyclohexane), m.p. 63°C.

This same compound is prepared in a yield of 55 % by the action of ethyl-2-bromobutyrate on 2-(2,3-dihydroxypropylamino) -phenol (Method D): 4.8 g of a suspension of sodium hydride in oil are slowly added to a solution of 18 g of 2-(2,3-dihydroxypropylamino)-phenol in dimethylformamide, followed by the addition 30 minutes afterwards of 20 g of ethyl-2-bromobutyrate. The mixture is then heated for 2 hours to 60°C and then kept for a few hours at the reflux temperature of the solvent. The solvent is then eliminated under reduced pressure, the residue dissolved in chloroform and the organic phase washed with a normal aqueous solution of soda and then with water. After drying over magnesium sulphate, the chloroform is eliminated under reduced pressure and the crude product obtained is purified by recrystallisation from cyclohexane.

EXAMPLE 9

2-n-propyl-3-oxo-4-(2,3-dihydroxy propyl)-6-chloro-2,3-dihydro-1,4-benzoxazine

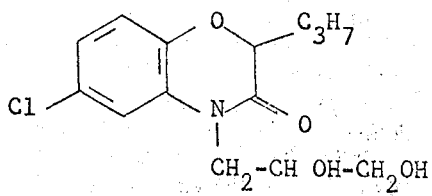

This compound is obtained in a yield of 50 % by Method A using dimethyl formamide as solvent (recrystallisation from isopropyl ether), m.p. 86°C.

EXAMPLE 10

2-ethyl-3-oxo-4-(2,3-dihydroxy propyl)-6-bromo-2,3-dihydro-1,4-benzoxazine

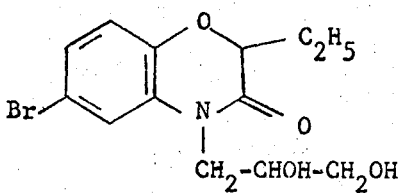

This compound is obtained in a yield of 50 % by Method A using ethanol as solvent (recystallisation from a mixture of benzene and petroleum ether (50 : 50), m.p. 91°C.

EXAMPLE 11

2-methyl-3-oxo-4-(2,3-dihydroxy propyl)-6-methoxy-2,3-dihydro-1,4-benzoxazine

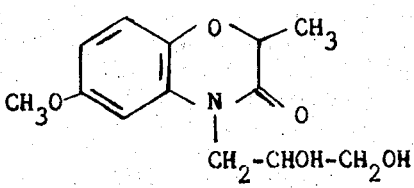

This compound is obtained in a yield of 40 % by Method A using ethanol as solvent (recystallisation from 1,2 dichloroethane), m.p. 70°C.

EXAMPLE 12

2-methyl-3-oxo-4-(2,3-dihydroxy propyl)-6-allyl-8-methoxy-2,3-dihydro-1,4-benzoxazine

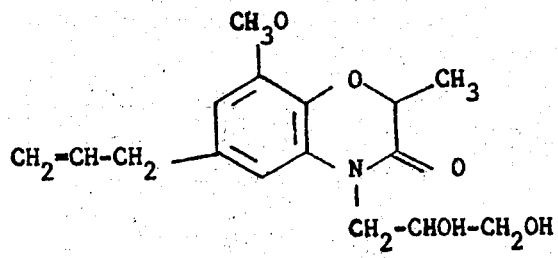

This compound is obtained in a yield of 65 % by Method A using ethanol as solvent (recystallisation from ethylacetate), m.p. 114-116°C.

EXAMPLE 13

2-n-butyl-3-oxo-4-(2,3-dihydroxy propyl)-6-chloro-2,3-dihydro-1,4-benzoxazine

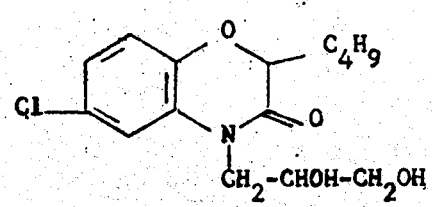

This compound is obtained in a yield of 50 % by Method A (recrystallisation from 1,2-dichloroethane), m.p. 69.5°C

EXAMPLE 14

2-methyl-3-oxo-4-(2,3-diacetoxy propyl)-6-chloro-2,3-dihydro-1,4-benzoxazine

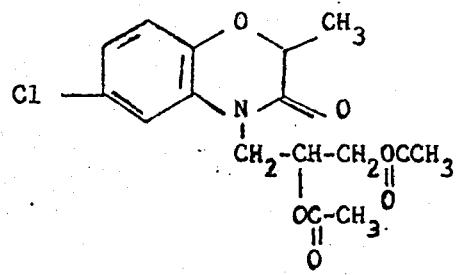

METHOD E 27.15 g of 2-methyl-3-oxo-4-(2,3-dihydroxy propyl)-6-chloro-2,3-dihydro-1,4-benzoxazine and 15 g of pyridine are introduced into 250 ml of anhydrous benzene, followed by the dropwise addition of 21 ml of acetic anhydride. After stirring for 5 hours at ambient temperature and for 1 hour at the reflux temperature of the solvent, the solution is poured into the same volume of ice water. The organic phase is decanted, washed with a solution of dilute hydrochloric acid and then liberally with water. After drying over sodium sulphate, the solvent is evaporated. The diester is obtained in a yield of 70 % (recrystallisation from a 50 : 50 ethanol : water mixture), m.p. 90°C.

EXAMPLE 15

2-ethyl-3-oxo-4-(2,3-diacetoxy propyl)-6-chloro-2,3-dihydro-1,4-benzoxazine

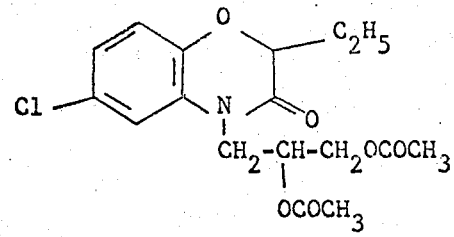

Method F 15.85 g of 2-ethyl-3-oxo-6-chloro-2,3-dihydro-1,4-benzoxazine are added to a solution of sodium ethylate in 100 ml of ethanol prepared with 1.8 g of sodium, and the mixture heated to its reflux temperature for 1 hour. 200 ml of dimethyl formamide are then added, and the ethanol evaporated under reduced pressure. 14.6 g of 1,2-diacetoxy-3-chloropropane are introduced into the medium and, after stirring for 2 hours at ambient temperature, the medium is heated slowly to a temperature of 80°C which is maintained for 2 hours until the medium is neutral. After filtration of the sodium chloride formed, the solvent is evaporated under reduced pressure. The diester which is unstable to distillation can be purified by chromatography in a silica column (eluent mixtures of chloroform and ether in variable proportions). Yield 40 %, the compound does not crystallise.
$n_D^{25} = 1.528$

EXAMPLE 16

3-oxo-4-(2,3-diacetoxy propyl)-6-chloro-2,3-dihydro-1,4-benzoxazine

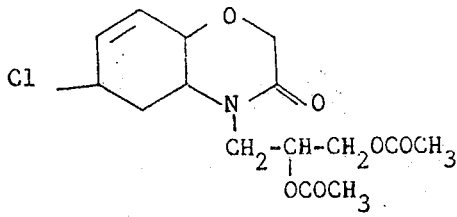

This product is obtained in a yield of 90 % by Method E. An oil is obtained, being purified by chromatography in a silica column (eluent: a mixture of chloroform and ether in variable proportions).
$n_D^{25} = 1.533$ The results of pharmacological tests carried out with the compounds according to the invention are summarised in the following. The test procedures adaopted were as follows:

1. Acute toxicity

The lethality of the products in a gummy suspension was determined following the oral administration of doses of 20 ± 2 g to random batches of 10 to 20 male mice. The calculations were made in accordance with Bliss's method (Quart. J. Pharm. Pharmacol., 2, 192–216).

2. Analgesic activity

Eddy's test in mice

Pain is induced by heat contact stimulation (mice placed on a heating plate kept at 56.5°C) and the time taken to react to the stimulus (licking of the front paws) is measured.

Batches of 10 animals selected at random are examined 30 minutes after the oral administration of the product to be tested in a gummy suspension.

The percentage of analgesic activity is established by taking as 100% activity the average response time of the control animals increased by 10 seconds.

Koster's test on mice

The pain is induced by the intraperitoneal injection of 0.10 ml/10 g of a 3% acetic acid solution.

The painful crises thus obtained (writhing of the trunk, stretching of the hind legs) are counted for 20 minutes following the injection.

The product to be tested was administered 30 minutes before the pain had been induced in batches of 10 male mice distributed at random. The percentage of analgesic activity is represented by the percentage decrease in the number of reactions established in relation to the controls.

3. ANTI-OEDEMATOUS ACTIVITY

Kaolin oedema in rats in accordance with WILHELMI AND DOMENJOZ

The product to be tested was orally administered to batches of 8 male rats distributed at random 30 minutes before the intraplantar injection of 0.15 ml. of a 10% kaolin suspension.

The volume of the paw is measured by plethysmography 5 hours after injection of the irritant. For each rat, the percentage oedema is evaluated in relation to the initial volume.

The percentage activity corresponds to the percentage decrease in oedema (average oedema of the treated animals in comparison with the average oedema of the control animals).

The results are set out in Tables I, II and III. Tables I and II relate to the toxicity and analgesic activity of the various products tested.

It can be seen in Table I that, in the two tests relating to analgesic activity, the compounds according to the invention which were studied have $ED_{50}$-values (per os) of less than or equal to 300 mg/kg. Table II also relates to the toxicity and analgesic activity of the products according to the invention. It is distinguished from Table I in that analgesic activity is expressed in percent, the animals having been given oral doses of 200 and 400 mg/kg.

The derivatives according to the invention show considerable antalgic power which is at least equivalent to that of amidopyrine and which can reach as much as five times the activity of this reference product. This is the case in particular with 2-methyl-3-oxo-4-(2,3-dihydroxypropyl)-6-chloro-2,3-dihydro-1,4-benzoxazine and with 2-ethyl-3-oxo-4-(2,3-dihydroxypropyl)-6-chloro-2,3-dihydro-1,4-benzoxazine which have $ED_{50}$-values of 60 mg/kg (per os) both with respect to the heat stimulus and with respect to the chemical stimulus.

The results relating to anti-oedematous activity are set out in Table III in which they are compared with the results obtained with a reference anti-inflammatory, namely phenylbutazone. In order to complete the comparison data, the $DL_{50}$-values (per os) in mice are also quoted.

The product of Example 3, namely 3-oxo-4-(2,3-dihydroxypropyl)-6-chloro-2,3-dihydro-1,4-benzoxazine is particularly interesting it proved to be antalgic both in Eddy's test ($ED_{50} = 200$ mg/kg per os) and in Koster's test ($ED_{50} = 100$ mg/kg per os) and anti-oedematous in Wilhelmi and Domenjoz's test ($ED_{50} = 200$ mg/kg per os) in which its activity is comparable with that of phenylbutazone.

TABLE I:

| Example No. | $DL_{50}$ per os (mg/kg/ in mice) | $ED_{50}$ Eddy's test (mg/kg) | $ED_{50}$ Koster's test (mg/kg) |
|---|---|---|---|
| 1 | 850 | 63 | 57 |
| 2 | 1660 | 61 | 60 |
| 3 | 1700 | 200 | 100 |
| 7 | >1000 | 300 | 300 |
| 9 | >1500 | 100 | 80 |
| 10 | >1500 | 200 | 300 |
| 12 | >1500 | 300 | 300 |
| 13 | 1500 | 100 | 100 |
| Amido-pyrine | 1850 | 300 | 120 |

TABLE II:

| Example No. | $DL_{50}$ mg/kg per os in mice | Eddy's test | Koster's test |
|---|---|---|---|
| | | % activity at 400 mg/kg per os | |
| 4 | >1500 | 42% | 68% |
| 5 | >1500 | 60% | 66% |
| 6 | >1500 | 52% | 46% |
| 14 | >1500 | 43% | 35% |
| 16 | >1500 | 28% | 51% |

% activity at 200 mg/kg per os*

TABLE II:-continued

| Example No. | DL₅₀ mg/kg per os in mice | Eddy's test | Koster's test |
|---|---|---|---|
| | | \% activity at 400 mg/kg per os | |
| 8 | 1200 | 5% | 21% |
| 11 | >1000 | 16% | 10% |
| 15 | >1500 | 14% | 20% |

*Dose administered when the 400 mg/kg dose produces signs of toxicity

TABLE III:

| Example No. | DL₅₀ mg/kg per os in mice | Kaolin oedema test ED₅₀ mg/kg per os |
|---|---|---|
| 3 | 1700 | 200 |
| 7 | >1000 | 400 |
| 11 | >1000 | 200 |
| 14 | >1500 | 400 |
| 15 | >1500 | 400 |
| 16 | >1500 | 400 |
| Phenylbutazone | 540 | 200 |

The new 3-oxo-1,4-benzoxazine derivatives are suitable for use as medicaments. They can be administered in combination with a physiologically acceptable vehicle, for example orally, rectally or parenterally.

The daily dose for adults can amount to between 3 and 6 tablets each containing 300 mg of active substance, or to between 2 and 4 suppositories each containing 500 mg.

Ampoules can contain from 25 to 150 mg of active substance.

We claim

1. Derivative of 3-oxo-2,3-dihydro-1,4-benzoxazine corresponding to the formula (I)

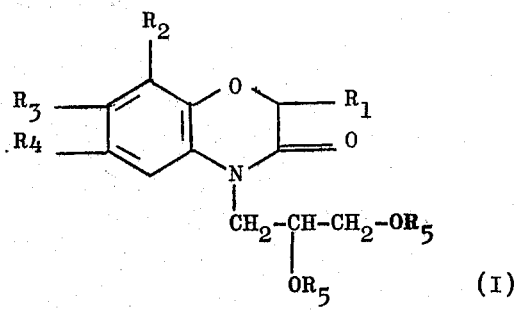

(I)

in which:

$R_1$ is selected from the group consisting of the hydrogen atom and a lower alkyl group; $R_2$, $R_3$ and $R_4$, which are identical or different, are selected from the group consisting of the hydrogen atom, a halogen atom, a nitro group, a lower alkyl group, a lower alkoxy group and $R_4$ may be an allyl group; and $R_5$ is selected from the group consisting of the hydrogen atom and an acetyl group.

2. 2-Methyl-3-oxo-4-(2,3-dihydroxypropyl)-6-chloro-2,3-dihydro-1,4-benzoxazine.

3. 2-Ethyl-3-oxo-4-(2,3-dihydroxypropyl)-6-chloro-2,3-dihydro-1,4-benzoxazine.

4. 3-Oxo-4-(2,3-dihydroxypropyl)-6-chloro-2,3-dihydro-1,4-benzoxazine.

5. 2-Methyl-3-oxo-4-(2,3-dihydroxypropyl)-6-chloro-7-bromo-2,3-dihydro-1,4-benzoxazine.

6. 2-Methyl-3-oxo-4-(2,3-dihydroxypropyl)-6-methyl-2,3-dihydro-1,4-benzoxazine.

7. 2-Methyl-3-oxo-4-(2,3-dihydroxypropyl)-6-n-propyl-8-methoxy-2,3-dihydro-1,4-benzoxazine.

8. 2-Methyl-3-oxo-4-(2,3-dihydroxypropyl)-6-nitro-2,3-dihydro-1,4-benzoxazine.

9. 2-Ethyl-3-oxo-4-(2,3-dihydroxypropyl)-2,3-dihydro-1,4-benzoxazine.

10. 2-n-Propyl-3-oxo-4-(2,3-dihydroxypropyl)-6-chloro-2,3-dihydro-1,4-benzoxazine.

11. 2-Ethyl-3-oxo-4-(2,3-dihydroxypropyl)-6-bromo-2,3-dihydro-1,4-benzoxazine.

12. 2-Methyl-3-oxo-4-(2,3-dihydroxypropyl)-6-methoxy-2,3-dihydro-1,4-benzoxazine.

13. 2-Methyl-3-oxo-4-(2,3-dihydroxypropyl)-6-allyl-8-methoxy-2,3-dihydro-1,4-benzoxazine.

14. 2-n-Butyl-3-oxo-4-(2,3-dihydroxypropyl)-6-chloro-2,3-dihydro-1,4-benzoxazine.

15. 2-Methyl-3-oxo-4-(2,3-diacetoxypropyl)-6-chloro-2,3-dihydro-1,4-benzoxazine.

16. 2-Ethyl-3-oxo-4-(2,3-diacetoxypropyl)-6-chloro-2,3-dihydro-1,4-benzoxazine.

17. 3-Oxo-4-(2,3-diacetoxypropyl)-6-chloro-2,3-dihydro-1,4-benzoxazine.

* * * * *